United States Patent
Ford

(10) Patent No.: US 11,571,414 B2
(45) Date of Patent: Feb. 7, 2023

(54) METHODS OF TREATING RESPIRATORY ILLNESSES, ALLEVIATING INFLAMMATION AND VISCERAL PAIN, AND ALLEVIATING OPIOID ADDICTION WHILE SUPPRESSING WITHDRAWAL SYMPTOMS

(71) Applicant: Eric Dawayne Ford, Canal Winchester, OH (US)

(72) Inventor: Eric Dawayne Ford, Canal Winchester, OH (US)

(73) Assignees: Eric Dwayne Ford, Canal Winchester, OH (US); Andrew Zock, Union Town, PA (US)

( * ) Notice: Subject to any disclaimer, the term of this patent is extended or adjusted under 35 U.S.C. 154(b) by 0 days.

(21) Appl. No.: 17/013,623

(22) Filed: Sep. 6, 2020

(65) Prior Publication Data
US 2021/0069168 A1 Mar. 11, 2021

Related U.S. Application Data

(60) Provisional application No. 62/896,942, filed on Sep. 6, 2019.

(51) Int. Cl.
*A61K 31/4468* (2006.01)
*A61K 9/70* (2006.01)

(52) U.S. Cl.
CPC ........ *A61K 31/4468* (2013.01); *A61K 9/7023* (2013.01)

(58) Field of Classification Search
CPC ................................................ A61K 31/4468
See application file for complete search history.

(56) References Cited

U.S. PATENT DOCUMENTS

| | | |
|---|---|---|
| 2018/0360821 A1 | 12/2018 | Laffont et al. |
| 2019/0054080 A1 | 2/2019 | Fischer |
| 2019/0152982 A1 | 5/2019 | Zhang et al. |
| 2019/0189257 A1 | 6/2019 | Rod |
| 2019/0201344 A1 | 7/2019 | Hayward et al. |
| 2019/0209427 A1 | 7/2019 | Warlick et al. |

OTHER PUBLICATIONS

Cichewicz et al (European Journal of Pharmacology 525 (2005) 74-82). (Year: 2005).*
Manral et al (Drug and Chemical Toxicology, vol. 32, 2009, Iss 2). (Year: 2009).*
Florence CS, Zhou C, Luo F, Xu L. The Economic Burden of Prescription Opioid Overdose, Abuse, and Dependence in the United States, 2013. Med Care. 2016; 54(10):901-906.

* cited by examiner

*Primary Examiner* — Benjamin J Packard
(74) *Attorney, Agent, or Firm* — Blynn L. Shideler; Krisanne Shideler; BLK Law Group

(57) ABSTRACT

The present invention provides a method of treating a respiratory illness in a subject in need thereof, comprising administering to the subject a therapeutically effective amount of a compound comprising a reaction product of a reaction mixture comprising: a) N-phenyl-N-[1-(2-phenyl-ethyl)piperidin-4-yl]propanamide or a derivative thereof; and b) dimethyl sulfoxide. Also provided are methods of alleviating opioid addiction while suppressing withdrawal symptoms and alleviating inflammation and visceral pain with minimal risk of addiction in a subject in need thereof, comprising administering to the subject a therapeutically effective amount of the compound described above.

14 Claims, No Drawings

METHODS OF TREATING RESPIRATORY ILLNESSES, ALLEVIATING INFLAMMATION AND VISCERAL PAIN, AND ALLEVIATING OPIOID ADDICTION WHILE SUPPRESSING WITHDRAWAL SYMPTOMS

CROSS REFERENCE TO RELATED APPLICATIONS

This application claims priority to provisional U.S. Patent Application Ser. No. 62/896,942, filed Sep. 6, 2019, and titled "METHODS OF ALLEVIATING INFLAMMATION AND VISCERAL PAIN AND ALLEVIATING OPIOID ADDICTION WHILE SUPPRESSING WITHDRAWAL SYMPTOMS", which is incorporated herein by reference in its entirety.

BACKGROUND OF THE INVENTION

Field of the Invention

The present invention relates to methods of treating respiratory illnesses such as COVID-19. The present invention also relates to methods of alleviating inflammation and visceral pain with minimal risk of addiction to opioids. The present invention additionally relates to methods of alleviating opioid addiction while suppressing withdrawal symptoms.

Background Information

In concert with the development of a vaccine for COVID-19, there has been implementation of therapeutic protocols that address particularly harmful symptoms, often those that are the most life-threatening in critical patients. A need exists for therapies that alleviate respiratory distress and inefficiencies of the lungs due to complications of COVID-19 infection and other respiratory illnesses or for any respiratory deficiency.

In other medical settings, opioids are widely used clinically to treat moderate to severe pain, particularly during recovery periods after surgical procedures. Opioids are chemical compounds that act on opioid receptors to produce morphine-like effects in the body. However, opioid analgesics suffer from major drawbacks. Prolonged opioid analgesic use can lead to dependence, which gives rise to withdrawal symptoms if the opioid analgesic treatment is stopped abruptly, such as when a prescription is depleted or expired. This opioid dependence can make opioid analgesics very addictive and subject to abuse. In addition, opioid analgesics are well known for their ability to produce a feeling of euphoria, motivating some to use opioids recreationally.

Opioid analgesic addiction is a major worldwide problem that is indiscriminate with respect to age, sex, race, or financial demographics. In 2015, two million Americans reported having a substance use disorder involving prescription pain relievers and 591,000 reported a substance disorder involving heroin. That number (2.591 million people) climbed to 5.1 million Americans by 2019. Moreover, the current opioid epidemic has been described as the deadliest drug crisis in American history, with an estimate of 130 people in the United States dying every day from overdosing on opioids. See CDC/NCHS, National Vital Statistics System, Mortality. CDC WONDER, Atlanta, Ga.: US Department of Health and Human Services, CDC; 2018. https://wonder.cdc.gov. Overdoses caused by opioids are the leading cause of death for Americans under the age of 50. The Centers for Disease Control and Prevention estimates that the total "economic burden" of prescription opioid misuse alone in the United States is $78.5 billion a year, including the costs of healthcare, lost productivity, addiction treatment, and criminal justice involvement. See Florence CS, Zhou C, Luo F, Xu L. The Economic Burden of Prescription Opioid Overdose, Abuse, and Dependence in the United States, 2013. Med Care. 2016; 54(10):901-906.

Efforts to minimize addiction have included the development of methadone, which activates opioid receptors and is administered through a once-daily serum. Buprenorphine also activates opioid receptors and is administered orally through pills or film, or by intravenous injection. Naltrexone binds to opioid receptors, blocking the total effects of an opioid. AT-121 is an experimental analgesic designed to be bifunctional, acting as an agonist at both the µ-opioid receptor and the nociception receptor. The interaction with the nociceptin receptor is believed to block the dependence-related side effects that are typical of opioids. A study in nonhuman primates found that AT-121 has morphine-like analgesic effects, but suppresses the addictive effects.

U.S. Patent publication 2019-0209427 teaches a method of treating a patient addicted to pain medication or opioids essentially by administering acoustic shock waves or pressure pulses to the patient.

U.S. Patent publication 2019-0201344 teaches compositions that are constructed to deliver naloxone as an injectable in-situ drug for extended release emergency treatment of opioid overdose.

Patent publication 2019-0189257 teaches a method for reducing addiction to opioids which advocates opioid reduction with assistance of proper use of medical cannabis by 1-3 g per day (maximum 5 g per day) which is alleged to reduce opioids by increments of 10%. Essentially in the opioid reduction plan of this disclosure the opioid is gradually replaced with medical cannabis.

Patent publication 2019-0152982 teaches compounds used in the treatment of opioid addiction and other diseases and conditions, including for the treatment of pain. The compounds are described as selective, reversible antagonists of the mu opioid receptor (MOR) that exhibit good blood brain barrier penetration.

Patent publication 2019-0054080 teaches pharmaceutical compositions for the treatment of opioid dependency comprising microparticles of a pharmacologically-effective amount of buprenorphine, or a pharmaceutically-acceptable salt thereof.

Patent publication 2018-0360821 teaches sustained-release buprenorphine formulations that produce therapeutic plasma concentration levels of buprenorphine in patients to treat opioid use disorder.

The above-identified patent applications are incorporated herein by reference. It would be desirable to provide a method of treating respiratory illnesses. It would further be desirable to provide a method of alleviating both pain and opioid addiction while suppressing withdrawal symptoms, preventing opioid dependence without the historical side effects of withdrawal.

SUMMARY OF THE INVENTION

The present invention provides a method of treating a respiratory illness in a subject (i. e., a human patient) in need thereof, comprising administering to the subject a therapeutically effective amount of a compound comprising a reaction product of a reaction mixture comprising:

a) N-phenyl-N-[1-(2-phenylethyl)piperidin-4-yl]propanamide (i. e., fentanyl) or a derivative thereof; and b) dimethyl sulfoxide.

The present invention further provides a method of alleviating opioid addiction while suppressing withdrawal symptoms in a subject in need thereof, comprising administering to the subject a therapeutically effective amount of a compound comprising a reaction product of the compound described above.

Also provided is a method of alleviating inflammation and visceral pain with minimal risk of addiction in a subject in need thereof, comprising administering to the subject a therapeutically effective amount of the compound described above.

In certain examples of the methods of the present invention, the compound may comprise a reaction product of a reaction mixture comprising:

a) N-[4-(methoxymethyl)-1-(2-phenylethyl)piperidin-4-yl]-N-phenyl-propanamide (also called 4-methoxy-methyl-fentanyl or R-30490); and b) dimethyl sulfoxide.

In certain examples of the methods of the present invention, the dimethyl sulfoxide may be present in the reaction mixture in a stoichiometric excess.

The compound may be administered to the subject transdermally, wherein the compound is administered to the subject in the form of an adhesive transdermal patch. Alternatively, the compound may be administered to the subject topically in the form of a liquid, cream, gel, fluid, lotion, emulsion or microemulsion.

The present invention also provides a compound for alleviating opioid addiction while suppressing withdrawal symptoms in a subject in need thereof, comprising a reaction product of a reaction mixture comprising:

a) N-phenyl-N-[1-(2-phenylethyl)piperidin-4-yl]propanamide or a derivative thereof; and b) dimethyl sulfoxide.

These and other advantages of the present invention will be clarified in the detailed description of the preferred embodiments.

DETAILED DESCRIPTION

Other than in the operating examples, or unless otherwise expressly specified, all of the numerical ranges, amounts, values and percentages in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Plural referents as used herein encompass singular and vice versa. For example, while the invention has been described in terms of "a" reaction product of a reaction mixture, a plurality, including a mixture of such reaction products can be used.

In the methods of the present invention, a therapeutically effective amount of a compound is administered to a subject in need of such therapy. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disorder being treated.

Subjects who may be treated by the method of the present invention include patients who present with respiratory distress and/or who have been diagnosed with a respiratory illness such as COVID-19, severe acute respiratory syndrome TSARS), influenza, pneumonia, tuberculosis, chronic bronchitis, emphysema, asthma, lung cancer, pulmonary fibrosis, cystic fibrosis, COPD, BOOP disease, and the like. The phrase "respiratory illness" is intended to be inclusive of all patients having respiratory deficiency or distress.

The compounds used in the therapeutic methods of the present invention comprise a reaction product of a reaction mixture comprising:

a) N-phenyl-N-[1-(2-phenylethyl)piperidin-4-yl]propanamide (fentanyl) or a derivative thereof; and b) dimethyl sulfoxide (DMSO). A "derivative thereof" may include chemically derived compounds as understood in the art or isomers of such derivatives. Examples of suitable derivatives of fentanyl may include 2,5-dimethylfentanyl, 3-allylfentanyl, p-fluoroisobutyrfentanyl, p-chloroisobutyrfentanyl, cyclopentylfentanyl, furanylethylfentanyl, methoxyacetylfentanyl, thenylfentanyl, 4-fluorobutyrfentanyl, 4-phenylfentanyl, valerylfentanyl, α-methylacetylfentanyl, al phamethyl butyrlf entanyl, alfentanyl, alphamethylthiofentanyl, α-methyl-thiofentanyl, alfentanil, butyrfentanyl (butyrylfentanyl), brifentanil (a-3331), isobutyrfentanyl, furanylfentanyl, N-methylcarfentanil, mirfentanil, N-[4-(methoxymethyl)-1-(2-phenylethyl)piperidin-4-yl]-N-phenyl-propanamide (R-30490, also known as 4-methoxymethylfentanyl), ohmefentanyl (also known as β-hydroxy-3-methylfentanyl, OMF and RTI-4614-4), 3-(4-(2-ethoxy-2-phenylethyl)piperazin-1-yl)-2-methyl-1-phenylpropan-1-one (eprazinone), ocfentanil, remifentanil, and/or sufentanil. Note that the phrase "and/or" when used in a list is meant to encompass alternative embodiments including each individual component in the list as well as any combination of components. For example, the list "A, B, and/or C" is meant to encompass seven separate embodiments that include A, or B, or C, or A+B, or A+C, or B+C, or A+B+C.

N-[4-(methoxymethyl)-1-(2-phenylethyl)piperidin-4-yl]-N-phenyl-propanamide (R-30490) may be particularly suitable in the formation of the reaction products used in the methods of the present invention.

The compounds (reaction products) are used as a pharmaceutical preparation in the methods of the present invention and are believed to offer numerous therapeutic benefits, including increased oxygen uptake (and hence oxygen levels) in the bloodstream, alleviating inflammation and visceral pain with minimal risk of addiction; alleviating opioid addiction while suppressing withdrawal symptoms; healing traumatized skin and vascular tissue; and healing scar tissue. The compounds have not been observed to behave as opioid suppressors or blockers.

The compounds used in the methods of the present invention may be administered by any conventional means of administration including, but not limited to, oral, nasal, pulmonary, sublingual, ocular, transdermal, rectal, vaginal and parenteral (i.e. subcutaneous, intramuscular, intradermal, intravenous etc.). While formulating a pharmaceutical preparation for use in the methods of the present invention in liquid dosage form for oral, topical and parenteral administration, any conventional pharmaceutical carriers or adjuvants may be employed. For liquid dosage forms such as suspensions (i.e. colloids, emulsions and dispersions) and solutions, suitable carriers and additives include one or more of pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle, typically water or an aqueous syrup, may be employed.

In solid oral preparations such as, for example, dry powders for reconstitution or inhalation, granules, capsules, caplets, gelcaps, pills and tablets (each including immediate release, timed release and sustained release formulations), suitable carriers and additives include diluents, granulating agents, lubricants, binders, disintegrating agents and the like. Tablets may be sugar coated, gelatin coated, film coated or enteric coated by known techniques.

In particular examples of the present invention, the reaction product is administered to the subject transdermally, such as in the form of an adhesive transdermal patch or topically in the form of a liquid, cream, gel, fluid, lotion, emulsion or micro-emulsion.

The pharmaceutical preparations contain per dosage unit, e.g., tablet, capsule, powder, injection, patch and the like, an amount of the active ingredient (reaction product) necessary to deliver an effective dose as described above. A typical dosage unit may range from 0.01 mg/kg to 300 mg/kg, such as 0.01 mg/kg to 100 mg/kg, or 0.01 mg/kg to 30 mg/kg and may be given at a dosage of from 0.01 mg/kg/day to 300 mg/kg/day (such as 0.01 mg/kg/day to 100 mg/kg/day or from 0.01 mg/kg/day to 30 mg/kg/day). The dosages may be varied depending upon the requirement of the subjects, the severity of the condition being treated and the compound being employed. The use of either daily administration or post-periodic dosing may be employed.

Optimal dosages to be administered may be readily determined by those skilled in the art, and will vary with the particular compound used, the mode of administration, the strength of the preparation, and the advancement of the disease/disorder condition. In addition, factors associated with the particular subject being treated, including subject age, weight, diet and time of administration, will result in the need to adjust the dose to an appropriate therapeutic level.

As noted above, the reaction mixture used to prepare the compounds that are utilized in the methods of the present invention further comprises b) dimethyl sulfoxide (DMSO). The dimethyl sulfoxide serves as a reactant, and may be present in the reaction mixture in stoichiometric excess relative to the fentanyl or derivative thereof, particularly in examples of the invention where the pharmaceutical preparation is to be administered transdermally. This allows for excess DMSO to be present in admixture with the reaction product, to enhance penetration of the reaction product through the skin. Alternatively, the DMSO may be present in the reaction mixture in stoichiometric equality relative to the fentanyl or derivative thereof, or any excess may be removed after reaction to purify/isolate the reaction product. This is particularly useful in examples of the invention where the pharmaceutical preparation is to be administered orally.

The pharmaceutical preparation may further comprise one or more additional penetration enhancers for transdermal drug delivery. Examples of additional penetration enhancers include $C_8$-$C_{22}$ fatty acids such as isostearic acid, octanoic acid, myristic acid and oleic acid; $C_8$-$C_{22}$ fatty alcohols such as oleyl alcohol and lauryl alcohol; lower alkyl esters of $C_8$-$C_{22}$ fatty acids such as ethyl oleate, isopropyl myristate (IPM), butyl stearate, and methyl laurate; di(lower)alkyl esters of $C_6$-$C_{22}$ diacids such as diisopropyl adipate; monoglycerides of $C_8$-$C_{22}$ fatty acids such as glyceryl monolaurate; tetrahydrofurfuryl alcohol polyethylene glycol ether; polyethylene glycol, propylene glycol; 2-(2-ethoxyethoxy)ethanol (transcutol); diethylene glycol monomethyl ether; alkylaryl ethers of polyethylene oxide; polyethylene oxide monomethyl ethers; polyethylene oxide dimethyl ethers; glycerol; ethyl acetate; acetoacetic ester; N-alkylpyrrolidone; and terpenes.

The therapeutic methods of the present invention may also be used in conjunction with other therapies. For example, in treating a respiratory illness, the method of the present invention may be used simultaneously or in sequence with other therapies. In the treatment of COVID-19 patients, the method of the present invention may be combined with the use of a respirator and/or in combination with zinc therapy, hydroxychloroquine, azithromycin-type antibiotics, Veklury™ based treatment, plasma therapy, MK-4482 based antiviral treatment, and/or other therapies.

In an alternative embodiment of the present invention the compounds used in the therapeutic methods of the present invention may comprise those having the following chemical structure:

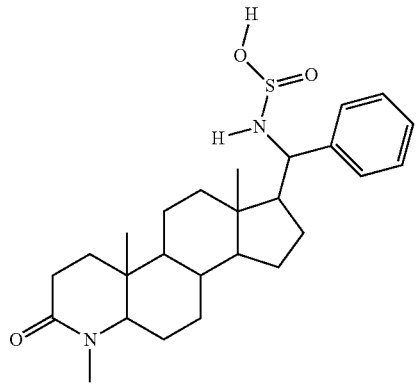 [SMILES: CN1C(=O)CCC2(C)C3CCC4(C)C(C(NS(=O)O)c5ccccc5)CCC4C3CCC12]

and/or with a chemical formula of $C_{26}H_{38}N_2O_3S$.

The compounds used in the methods of the second embodiment of the present invention may also be administered by any conventional means of administration including, but not limited to, oral, nasal, pulmonary, sublingual, ocular, transdermal, rectal, vaginal and parenteral (i.e. subcutaneous, intramuscular, intradermal, intravenous etc.) as detailed above.

Though not intending to be bound by theory, it is believed that the compounds used in the methods of the present invention address withdrawal symptoms by allowing the µ-opioid receptor and the nociceptin receptor agonist an extended stay within the body's ecosystem through tubular reabsorption. It is further believed that the compounds used in the methods of the present invention increase oxygen levels in the bloodstream by improving oxygen uptake in the bloodstream.

The example below illustrates the preparation of a reaction product useful in the methods of the present invention. Note that the use of any other compounds listed above in such a preparation process would be expected to provide similar results.

EXAMPLE

A reaction mixture was prepared at room temperature and atmospheric pressure as follows: a 1000 ml solution of DMSO and distilled water was prepared (80 percent by volume DMSO/20 percent by volume water; note that the volume ratio of DMSO to water may typically range from 70:30 to 90:10) in a flask and stirred vigorously for 30 minutes to ensure homogeneity. 50 g of R-30490 was added dropwise (note that any amount from, for example, 25 to 100 g may be added) and allowed to settle to the bottom, after which the mixture was stirred vigorously with a cobalt metal stirrer until none of the R-30490 was noticeable in the flask. The mixture was allowed to sit for one hour to yield a reaction product in accordance with the present invention.

Whereas particular examples of this invention have been described above for purposes of illustration, it will be evident to those skilled in the art that numerous variations of the details of the present invention may be made without departing from the scope of the invention as defined in the appended claims.

What is claimed is:

1. A method of treating a respiratory illness in a subject in need thereof, comprising administering to the subject a therapeutically effective amount of a compound comprising a reaction product of a reaction mixture comprising:
   a) N-phenyl-N-[1-(2-phenylethyl)piperidin-4-yl]propanamide or a derivative thereof; and
   b) dimethyl sulfoxide.

2. The method of claim 1 wherein the compound comprises a reaction product of a reaction mixture comprising:
   a) N-[4-(methoxymethyl)-1-(2-phenylethyl)piperidin-4-yl]-N-phenyl-propanamide; and
   b) dimethyl sulfoxide.

3. The method of claim 1 wherein the dimethyl sulfoxide is present in the reaction mixture in a stoichiometric excess.

4. The method of claim 3 wherein the compound is administered to the subject transdermally and wherein said method further comprises alleviating inflammation and visceral pain.

5. The method of claim 1 wherein the compound consists essentially of a reaction product of:
   a) N-phenyl-N-[1-(2-phenylethyl)piperidin-4-yl]propanamide or a derivative thereof; and
   b) dimethyl sulfoxide.

6. The method of claim 5 wherein the compound is administered to the subject orally and wherein said method increases oxygen uptake in the bloodstream and alleviates inflammation and visceral pain.

7. The method of claim 1 wherein the compound comprises a reaction product formed in the presence of cobalt.

8. A method of treating a respiratory illness in a subject in need thereof, comprising administering to the subject a therapeutically effective amount of a compound comprising a reaction product of a reaction mixture comprising:
   a) N-[4-(methoxymethyl)-1-(2-phenylethyl)piperidin-4-yl]-N-phenyl-propanamide; and
   b) dimethyl sulfoxide, wherein the dimethyl sulfoxide is present in the reaction mixture in a stoichiometric excess.

9. The method of claim 8 wherein the compound comprises a reaction product formed in the presence of cobalt.

10. The method of claim 9 wherein the compound consists essentially of a reaction product of:
    a) N-[4-(methoxymethyl)-1-(2-phenylethyl)piperidin-4-yl]-N-phenyl-propanamide; and
    b) dimethyl sulfoxide, wherein the dimethyl sulfoxide is present in the reaction mixture in a stoichiometric excess.

11. The method of claim 10 wherein the compound is administered to the subject orally and wherein said method increases oxygen uptake in the bloodstream and alleviates inflammation and visceral pain.

12. A method of treating a respiratory illness in a subject in need thereof, comprising administering to the subject a therapeutically effective amount of a compound consisting essentially of a reaction product of:
    a) N-[4-(methoxymethyl)-1-(2-phenylethyl)piperidin-4-yl]-N-phenyl-propanamide; and
    b) dimethyl sulfoxide.

13. The method of claim 12 wherein the compound comprises a reaction product formed in the presence of cobalt.

14. The method of claim 12 wherein the compound is administered to the subject orally and wherein said method increases oxygen uptake in the bloodstream and alleviates inflammation and visceral pain.

* * * * *